US010308976B2

(12) United States Patent
Van Meerbergen et al.

(10) Patent No.: US 10,308,976 B2
(45) Date of Patent: *Jun. 4, 2019

(54) SELECTIVE LYSIS OF CELLS

(75) Inventors: Bart Edward Jozef Gusta Van Meerbergen, AE Eindhoven (NL); Oana Mihaela Piciu, AE Eindhoven (NL); Ron Gill, AE Eindhoven (NL); Kristiane Anne Schmidt, AE Eindhoven (NL); Sieglinde Neerken, AE Eindhoven (NL); Marc Wilhelmus Gijsbert Ponjee, AE Eindhoven (NL); Zeynep Seflek, AE Eindhoven (FR); Roel Penterman, AE Eindhoven (NL); Paul Arnold Van De Wiel, AE Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/514,734

(22) PCT Filed: Dec. 7, 2010

(86) PCT No.: PCT/IB2010/055628
§ 371 (c)(1),
(2), (4) Date: Sep. 24, 2012

(87) PCT Pub. No.: WO2011/070507
PCT Pub. Date: Jun. 16, 2011

(65) Prior Publication Data
US 2013/0171615 A1 Jul. 4, 2013

(30) Foreign Application Priority Data
Dec. 7, 2010 (EP) ..................................... 09178363

(51) Int. Cl.
*C12N 1/06* (2006.01)
*C12Q 1/689* (2018.01)
*C12Q 1/6806* (2018.01)
*C12Q 1/6895* (2018.01)
*G01N 33/48* (2006.01)

(52) U.S. Cl.
CPC ............. *C12Q 1/6806* (2013.01); *C12N 1/06* (2013.01); *C12Q 1/689* (2013.01); *C12Q 1/6895* (2013.01); *G01N 33/48* (2013.01)

(58) Field of Classification Search
CPC .... C12Q 1/6806; C12Q 1/6895; C12Q 1/689; C12Q 2527/125; C12Q 2527/119; C12N 1/06
USPC .......................................................... 435/2
See application file for complete search history.

(56) References Cited

U.S. PATENT DOCUMENTS

| 6,632,399 B1 | 10/2003 | Kellogg et al. ................ 422/72 |
| 6,803,208 B2 | 10/2004 | Seaver et al. .................. 435/34 |
| 7,387,883 B2 | 6/2008 | Walsh et al. ................... 435/36 |
| 8,530,231 B2 | 9/2013 | Nakae et al. .............. 435/307.1 |
| 2008/0160528 A1 | 7/2008 | Lorenz .............................. 435/6 |

FOREIGN PATENT DOCUMENTS

| EP | 0 745 849 A2 | 12/1996 | ............. G01N 33/50 |
| JP | 7-509783 | 10/1995 | ........... G01N 33/543 |
| JP | 2007-502618 | 2/2007 | ............... C12Q 1/68 |
| JP | 2008-539712 | 11/2008 | ............... C12Q 1/04 |
| JP | 2008-298615 A | 12/2008 | ............. C12M 1/00 |
| JP | 2009-247250 A | 10/2009 | ............. C12M 1/00 |
| JP | 2012-507283 | 3/2012 | ............... C12Q 1/04 |
| JP | 2012-507710 | 3/2012 | ............. G01N 33/48 |
| JP | 2012-507712 | 3/2012 | ............. G01N 21/64 |
| JP | 2012-526996 | 11/2012 | ............. G01N 35/02 |
| WO | WO 86/00139 | 1/1986 | ............. G01N 33/50 |
| WO | WO 93/16384 | 8/1993 | ............. G01N 33/48 |
| WO | WO 94/10571 | 5/1994 | ............. G01N 33/53 |
| WO | WO 00/71675 | 11/2000 | ............... C12N 1/06 |
| WO | WO 00/72970 A1 | 12/2000 | ............... B01L 3/00 |
| WO | WO 03/035899 | 5/2003 | ............... C12Q 1/04 |
| WO | WO 2005/021799 | 3/2005 | ............... C12Q 1/68 |
| WO | WO 2005/068647 | 7/2005 | ............... C12Q 1/00 |
| WO | WO 2009/098104 | 8/2006 | ............... B01L 3/00 |
| WO | WO 2006/117557 | 11/2006 | ............... C12Q 1/06 |
| WO | WO 2008/000343 | 1/2008 | ............. C12N 15/00 |
| WO | WO 2008/078808 A1 | 7/2008 | ............. A61B 5/154 |
| WO | WO 2009/015484 | 2/2009 | ............... C21N 1/00 |
| WO | WO 2010/062349 | 6/2010 | ............. G01N 33/68 |
| WO | WO 2010/062351 | 6/2010 | ............. G01N 21/65 |
| WO | WO 2010/062356 | 6/2010 | ............. G01N 21/65 |
| WO | WO 2010/132823 | 11/2010 | ............. C12M 1/26 |

OTHER PUBLICATIONS

Peters et al., 2004, Lancet Infect. Dis., 4, 751-760 (Year: 2004).*
Brakstad et al., 1992, Journal of Clinical Microbiology, 30, 1654-1660 (Year: 1992).*
International Search Report for International Application No. PCT/IB2010/055628, dated Mar. 23, 2011.
International Preliminary Report on Patentability for International Application No. PCT/IB2010/055628, dated Jun. 12, 2012.
Sullivan et al., "Practical Aerobic Membrane Filtration Blood Culture Technique: Development of Procedure," Journal of Clinical Microbiology, American Society for Microbiology, Washington, DC, US, vol. 1, No. 1, Jan. 1, 1975, pp. 30-36, XP000645255, ISSN: 0095-1137, pp. 30-31.
Zierdt et al., "Development of a Lysis-Filtration Blood Culture Technique," Journal of Clinical Microbiology, American Society for Microbiology, Washington, DC, US, vol. 5, No. 1, Jan. 1, 1977, pp. 46-50, XP000645254, ISSN: 0095-1137, pp. 46-47, p. 48; col. 2, paragraph 2.

(Continued)

Primary Examiner — Sean C. Barron

(57) ABSTRACT

Methods and devices for the selective lysis of cells in a sample comprising micro-organisms such as bacteria are provided. The selective lysis is obtained by incubating the sample in a non-ionic detergent under alkaline conditions.

9 Claims, 7 Drawing Sheets

(56) References Cited

OTHER PUBLICATIONS

Brown et al., "Sorting of GPI-anchored Proteins to Glycolipid-enriched Membrane Subdomains during Transport to the Apical Cell Surface," Cell, Cell Press, Cambridge, NA, US LNKD-DOI:10.1016/0092-8674(92)90189-J, vol. 68, No. 3, Feb. 7, 1992, pp. 533-544, XP023884467, ISSN: 0092-8674, p. 542, col. 1, paragraph 3; table 1.

Harrison et al., "Bacterial Cell Disruption: A Key Unit Operation in the Recovery of Intracellular Products," Biotechnology Advances, Elsevier Publishing, Barking, GB, LNKD-DOI:10.1016/0734-9750(91)90005-G, vol. 9, No. 2, Jan. 1, 1991, pp. 217-240, XP000220253, ISSN: 0734-9750, p. 228, paragraph 6, p. 229, paragraph 1; figure 1.

Birnboim et al., "A Rapid Alkaline Extraction Procedure for Screening Recombinant Plasmid DNA," Nucleic-Acids Research, Oxford University Press, Surrey, GB, vol. 7, No. 6, Nov. 24, 1979, pp. 1513-1523, XP008104127, ISSN: 0305-1048, p. 1514, paragraph 2.

Handschur et al., "Preanalytic Removal of Human DNA Eliminates False Signals in General 16S rDNA PCR Monitoring of Bacterial Pathogens in Blood," Comparative Immunology, Microbiology and Infectious Diseases, Pergamon Press, Oxford, GB, LNKD-DOI:10.1016/J.CIMID.2007.10.005, vol. 32, No. 3, May 1, 2009, pp. 207-219, XP025966511, ISSN: 0147-9571, p. 210, paragraphs 3-4.

Zierdt, "Blood-Lysing Solution Nontoxic to Pathogenic Bacteria," Journal of Clinical Microbiology, vol. 15, No. 1, Jan. 1982, pp. 172-174.

Extract of laboratory notebook entry dated Jan. 13, 2015 containing test results following the lysis protocol as described in Example 6 of WO 2010/062356 A1, cited in EP Opposition to EP 2510123 B1 by bioMérieux, Inc, Jun. 24, 2015.

Website print out of "Sodium hydroxide," from Wikipedia, the free encyclopedia, en.wikipedia.org/wiki/Sodium_hydroxide, print out date Jun. 16, 2015.

Laboratory report showing pH of a lysis buffer/sample mixture of Example 1 of WO 2005/068647 A2 and of the Example in U.S. Pat. No. 7,387,883 B2, cited in EP Opposition to EP 2510123 B1 by bioMérieux, Inc, Jun. 24, 2015.

Website print out of "Sigma-Aldrich Biological Buffers, Buffer Reference Center," http://www.sigmaaldrich.com/life-science/core-bioreagents/biological-buffers/learning-center/buffer-reference-center.html, print out date Jun. 16, 2015.

Wu et al., "Preparation of milk samples for PCR analysis using a rapid filtration technique," *Journal of Applied Microbiology* 2004, 96, pp. 1342-1346.

\* cited by examiner

SELECTIVE LYSIS OF CELLS

FIELD OF THE INVENTION

The present invention relates to the lysis of eukaryotic cells, in particular animal cells, such as blood cells. The present invention further relates to the detection of low concentrations of micro-organisms such as bacteria in samples with high concentrations of other cells.

BACKGROUND OF THE INVENTION

Molecular diagnostics aims at the rapid detection of minute amounts of pathogens (typically bacteria) in samples such as blood. Blood is however a complex matrix and comprises white blood cells (leukocytes) for the adaptive immune system, red blood cells (erythrocytes) for oxygen transport, and platelets (thrombocytes) for wound healing. This complicates the direct detection of pathogens in samples such as whole blood, which contain a high amount of cellular material.

Classical detection methods comprise the growth of bacteria on selective media and/or media with indicators. Typically such assays require a cultivation step of at least 1 or 2 days before identification can take place.

For PCR based methods the amount of bacteria in a fresh blood sample is theoretically high enough to be detected without further cultivation of the bacteria present within such sample. However, to allow an early detection of minute amounts of bacteria, large volumes of blood are required. The high amount of DNA in especially white blood cells dramatically increases the background in DNA based detection methods. Also the presence of heme from hemoglobin strongly decreases the activity of DNA polymerase. A microliter of human blood contains about 4,000 to 11,000 white blood cells and about 150,000 to 400,000 platelets. The concentration of DNA in blood is between 30 and 60 µg/ml. It is extremely challenging to detect in a volume of 10 ml of whole blood the presence of about 10 to 100,000 of a bacterial species.

The high amounts of DNA of the white blood cells may give rise to non relevant PCR products, or may scavenge the primers designed for the detection of bacterial DNA. This necessitates a thorough DNA purification and separation of mammalian DNA before the bacterial DNA can be detected via PCR or other methods.

Apart from interfering with the PCR reaction itself the amount of mammalian DNA increases the viscosity of a sample. In addition, proteins and membranes from the lysed mammalian cells form complexes which prevent the filtration of a sample. This is particularly a problem for miniaturized devices. Further dilution of the, already large sample volume, results in unacceptable long manipulation steps.

For the above reasons, methods to remove human DNA from a blood sample are accordingly required.

Methods to specifically assay bacterial DNA in the presence of mammalian DNA are known. Looxter™ from the company SIRSLab uses a method to enrich methylated DNA from a sample. As bacterial DNA is strongly methylated, this approach results in an enrichment of bacterial DNA. Molysis™ from the company Molzym, uses chaotropic agents and detergents to lyse selectively mammalian cells. This lysis step is followed by a digest with a DNAse which is not affected by this chaotropic agent/detergent. Alternative approaches such as commercialized by Roche (Septifast™) rely on PCR primer pairs which are specifically designed to prevent aspecific binding to human DNA and amplification of human DNA.

U.S. Pat. No. 6,803,208 describes a method wherein a highly diluted suspension of blood platelets doped with bacteria is lysed at 37° C. for 15 minutes, whereafter it is possible to filter a small amount of the lysed sample over a 0.4 µm filter for visual inspection of the bacteria which are retained on the filter. This method however does not allow to process large volumes of sample at ambient temperatures.

SUMMARY OF THE INVENTION

Particular and preferred aspects of the invention are set out in the accompanying independent and dependent claims. Features from the dependent claims may be combined with features of the independent claims and with features of other dependent claims as appropriate and not merely as explicitly set out in the claims.

One aspect of the invention relates to a method for the selective lysis of eukaryotic cells, in particular animal cells, within a sample containing or suspected to contain a micro-organism. This method comprises the steps of providing a sample with eukaryotic cells, in particular animal cells, containing or suspected to contain a micro-organism, adding a non-ionic detergent and a buffer to the sample to obtain a solution with a pH of about 9.5 or more, and incubating the solution for a time period sufficiently long to lyse the eukaryotic cells, in particular animal cells, for example between 30 seconds and 10 minutes, more preferably between 2 and 6 minutes. The lysis can be performed in particular embodiments between 15 and 30° C., more preferably around room temperature.

In particular embodiments, the sample is a mammalian blood sample, such as whole blood.

In other particular embodiments the micro-organism is a bacterium or fungus.

According to particular embodiments, the ratio between the volume of added detergent and added buffer and the volume of sample is between 2/1 and 1/10.

In particular embodiments, the non-ionic detergent is selected from the group comprising Nonidet, Brij, Tween, Igepal, reduced triton, octylglucoside, cholaat and Triton. More preferred examples are Triton X-100, Nonidet P40, Sodium deoxycholate and or Igepal CA 630.

In particular embodiments, the alkaline buffer as used herein has a pKa value above 9. Examples hereof are borate, carbonate, CAPS(N-cyclohexyl-3-aminopropanesulfonic), CAPSO (3-(Cyclohexylamino)-2-hydroxy-1-propanesulfonic acid), CHES (2-(N-Cyclohexylamino)ethane Sulfonic acid), pyrophosphate and ethanolamine. A particular example is sodium carbonate. The buffer should have sufficient buffer capacity that when mixed with the sample in ratios according to the present invention, the pH of the final solution is around 9.5 or higher.

In particular embodiments, the method further comprises the step of filtering the incubated solution on a filter with a pore size which retains micro-organisms on the filter, such as a filter with a pore size of less than 0.7 µm, more preferably less than 0.5 µm. the method of the present invention facilitates the filtration of high volumes of sample without enzymatic or heat related process steps.

In particular embodiments, the method further comprises the step of adding after the selective lysis according to the invention an acid or acidic buffer to obtain a pH between about 7 and 9, a "neutralization step".

In particular embodiments, the methods as described above are followed by detection of the micro-organisms. Examples hereof are cytometry, microscopy, PCR or culturing.

In particular embodiments, the methods as described above are followed by lysis of micro-organisms.

Another aspect of the present invention relates to a device (1) for the detection of micro-organisms in sample, comprising: a lysis chamber (2) for accepting a sample fluid with a volume below 40 ml, preferably below 20 ml and more preferably between 1 and 20 ml, a reservoir (3) comprising an alkaline buffer with a pH of about 9.5 or more and comprising a non-ionic detergent, or a reservoir comprising an alkaline buffer (31) with a pH of about 9.5 or more, a reservoir comprising a non-ionic detergent (32), connected to the lysis chamber, a filter (4) connected to the lysis chamber for filtering the sample after lysis, the filter having a pore size which retains bacteria on the filter, and a detection chamber (5) for assaying the presence of DNA.

Herein the alkaline buffer has typically a pKa above 9.5 so the final solution will have a pH of about 9.5 or higher, and the non-ionic detergent is typically Triton X-100, Sodium deoxycholate, Nonidet P40 and/or Igepal CA 630.

Methods as described in the present invention allow a selective lysis of white and red blood cells in a sample while bacteria and fungi remain intact (either dead or alive).

Methods as described in the present invention make it possible to process a sample without substantially diluting such sample, and consequently allow to process larger volumes of sample. In addition, there is no need for enzymatic degradation of DNA by e.g. DNase or the use of heat, making this method less complex compared to methods known in the prior art.

Methods as described in the present invention result in lysed samples with a low viscosity and a minimum of aggregates, which makes it possible to filter large volumes of the lysed sample over a filter which retains bacteria. Further processing of the bacteria on such filter can proceed with volumes between about 100-1000 µl, which makes it possible to process large sample volumes for subsequent procedures and to perform the required manipulations, such as neutralization and washing, fully automated in an integrated cartridge.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
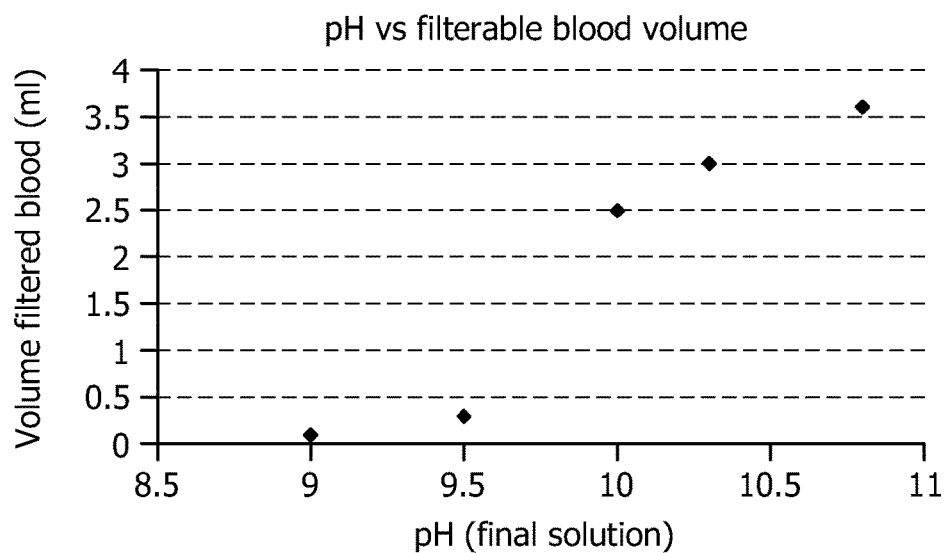
FIG. 1 shows the filtration efficiency of large volumes of blood after selective lysis at different pH values in accordance with a particular embodiment of methods of the invention.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. These definitions should not be construed to have a scope less than understood by a person of ordinary skill in the art.

DETAILED DESCRIPTION OF THE EMBODIMENTS

"Blood cells" in the context of the present invention relates to mammalian cells present in blood and includes red blood cells (erythrocytes), white blood cells (leukocytes) and blood platelets (thrombocytes).

"Whole blood" in the context of the present invention relates to unprocessed blood comprising blood plasma and cells, potentially treated with an anti-coagulant.

"Sample" relates to an aqueous suspension comprising cellular material and comprises body fluids such as lymph, cerebrospinal fluid, blood (whole blood and plasma), saliva, but also comprises e.g. the aqueous fraction of homogenized suspensions such as e.g. muscles, brain, liver, or other tissues.

"Eukaryotic" in the present invention relates to any type of eukaryotic organism excluding fungi, such as animals, in particular animals containing blood, and comprises invertebrate animals such as crustaceans and vertebrates. Vertebrates comprise both cold-blooded (fish, reptiles, amphibians) and warm blooded animal (birds and mammals). Mammals comprise in particular primates and more particularly humans.

"Selective lysis" as used in the present invention is obtained when in a sample (such as blood) the percentage of micro-organism cells (such as bacterial cells) in that sample that remain intact is significantly higher (e.g. 2, 5, 10, 20, 50, 100, 250, 500, or 1000 time more) compared to the percentage of the eukaryotic cells from the organism from which the sample is collected that remain intact.

"Micro-organism" as used in the present invention relates to bacteria (gram positive and gram negative bacteria, as well as bacterial spores) and unicellular fungi such as yeast and molds, which are present in the organism from which a sample has been collected, typically as a pathogen.

A first aspect of the present invention relates to a method for the selective lysis of eukaryotic cells, in particular animal cells, within a sample, which contains or is suspected to contain micro-organisms such as bacteria. The aim of the method is to increase the sensitivity of a test for the detection of minute amounts of bacteria in a sample (i.e. less than 10000, 1000, 100 or even less micro-organisms per ml of sample). As explained in the background of the invention, DNA from eukaryotic cells, in particular from animal cells, in a sample interferes with PCR based detection methods and this DNA, together with proteins and membranes form aggregates which increases viscosity after lysis and which has a dramatic impact on the filtration of a lysed sample. To solve this problem, the eukaryotic cells, in particular animal cells, are selectively lysed whereby a substantial part (i.e. more than 20%, 40%, 60%, 80%, 90% or even more that 95%) of the micro-organisms remains alive, or if killed by the treatment, still comprise the bacterial DNA within the cell wall. In methods as described in the present invention the above mentioned problems are addressed.

Methods as described in the present invention are particularly applicable to any type of sample wherein the detection of DNA from micro-organisms, particularly from bacteria, is impaired by the presence of other cells comprising DNA, in particular cells from a host wherein the micro-organism is present as a pathogen.

Methods as described in the present invention are now further illustrated for embodiments wherein the presence of minute amounts of bacteria in a mammalian blood sample is investigated.

The blood sample can be stored as whole blood or a processed fraction such as plasma or a platelet preparation. Typically, methods as described in the present invention are performed on freshly isolated whole blood. Such samples are generally treated with e.g. heparin, EDTA or citrate to avoid coagulation.

Alternatively the method is performed on fresh blood by collecting the blood from the vein directly in a tube with detergent and buffer.

Accordingly, a fresh blood sample or a preserved sample is supplemented with a buffer and a non-ionic detergent. The selection of the buffer and its concentration are chosen in order to compensate the buffering capacity of the blood sample provided and to obtain a pH around or higher than 9.5, more particular between 9.5 and 11.5, even more particular between 9.5 and 10.5. pH values above 11.5 are suitable for more robust organisms such as gram positive bacteria and fungi. Equally the buffer is sufficiently concentrated such that at most a buffer volume of 200%, 150%, 100%, 50%, 20% or 10% of the sample volume is added to the sample to obtain the required change in pH.

Suitable buffers in the context of the present invention typically have a pKa above 9, above 9.5 or even above 10 and include borate, carbonate, CAPS, CAPSO, CHES, pyrophosphate, ethanolamine, and other commonly used buffers with an optimal buffering capacity in the above mentioned pH ranges Suitable detergents are non-ionic detergents, which at the one hand have a lytic effect on the eukaryotic cells, in particular animal cells, only and on the other hand have a solubilising effect on DNA and proteins.

Examples of non-ionic detergents are alkylglycosides, Brij 35 (C12E23 Polyoxyethyleneglycol dodecyl ether) (15, 7), Brij 58 (C16E20 Polyoxyethyleneglycol dodecyl ether) (16), Genapol (13 to 19), glucanids such as MEGA-8, -9, -10, octylglucoside (12,6), Pluronic F127, Triton X-100 ($C_{14}H_{22}O(C_2H_4O)_n$) (13,4), Triton X-114 ($C_{24}H_{42}O_6$) (12, 4), Tween 20 (Polysorbate 20) (16, 7) and Tween 80 (Polysorbate 80) (15) Nonidet P40 sodium deoxycholate, reduced Triton X-100 and or Igepal CA 630. A particular preferred example of a non-ionic detergent is Triton-X 100.

The most effective concentration of detergent depends from detergent to detergent, but typically is within the range of between 0.1 and 5%, more particularly between 0.1 and 1%. Depending from the detergent (solid or liquid) % refers to respectively w/v % or v/v %.

The incubation of a blood sample in the presence of buffer and detergent is performed within 10 minutes, preferably between 30 seconds and 10 minutes and more preferably between about 1 to 3, 1-5,1-8, 2-6 or 1-10 minutes, at temperatures between 10 and 30° C., more preferably around room temperature.

Methods according to the present invention have the advantage that a selective lysis is obtained below 10 minutes, at temperatures below 30° C. Accordingly, the methods can be generally performed at ambient temperatures without the need to heat the sample.

Optionally, after the lysis the pH of the lysed sample is brought to a neutral value (i.e. between 7 and 9) by the addition of an acid or acidic buffer in a neutralization step. It was found that a lysed sample at neutral pH could be stored for a prolonged time (up to 1, 2, 6, 12 or even 24 hours) without further lysis of bacterial cells and without dramatic changes in the fluidic properties of the lysed sample.

Another parameter investigated in the methods of the present invention is the evaluation of the fluidic properties of the blood sample after lysis. This can be determined by verifying which volume of lysed blood can be filtered through a 0.22 μm filter. Methods in accordance with the present invention allow the filtration of at least 2, 5, 7, 5 or even 10 ml of whole blood which was diluted by addition of 1 volumes of buffer/detergent solution to 1 volume of sample.

Generally, methods in accordance with the present invention comprise a step wherein the intact bacterial cells are separated from the sample, typically performed by centrifugation or filtration. In particular embodiments intact bacteria are separated from the sample by passage of the lysed sample over a filter, with a pore size below 1 μm, to retain bacteria which have typically a size between 0.5 and 10 μm, such as commercially available filters with a pore size of 0.4 or 0.22 μm. For the filtration of samples, a wide variety of commercially available devices exists, such as filters adapted to fit on a syringe such that after lysis within in syringe, the fluid can be passed over the filter by manual pressure on the plunger of the syringe.

Hereafter the presence of bacteria (or fungi) on the filter can be investigated. In particular embodiments the presence of micro-organisms is investigated by PCR. For this purpose, bacteria (or fungi) can be washed away from the filter and further treated for PCR amplification. Alternatively the filter is rinsed with a lysis buffer to release the DNA from the micro-organisms, which is further used in a PCR reaction.

Other detection steps that can be performed by cytometry, microscopy, PCR or culturing.

Figure 11:
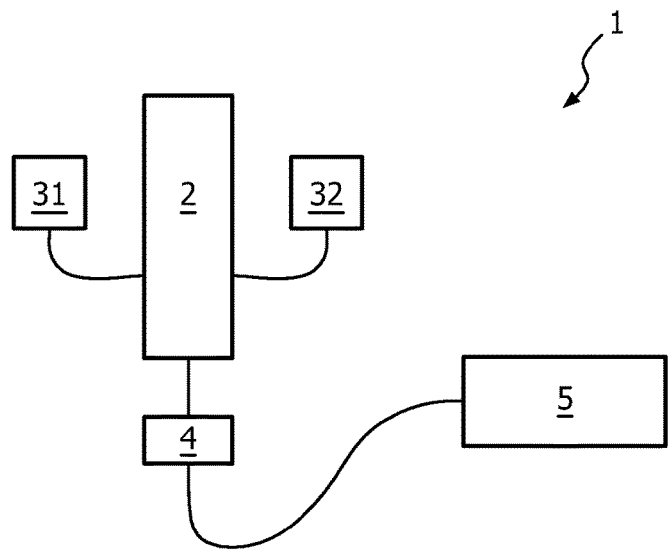
FIG. 11 shows a schematic overview of an embodiment of a device for performing a selective lysis as described in embodiments of the present invention.

The lysis of the sample, filtration and detection of micro-organisms can be performed within one device (schematically depicted in FIG. 11). Accordingly, one aspect of the present invention relates to a device (1), comprising a lysis chamber (2) for accepting a sample fluid with a volume between 1 and 10 ml, a reservoir (3) comprising an alkaline buffer with surfactants as described above, or a reservoir comprising an alkaline buffer (31) as described above and a reservoir comprising surfactants (32) as described above, the reservoirs connected to the lysis chamber (2). Within the device, the lysis chamber is connected to a filter (4) for filtering the sample after lysis whereby micro-organisms are retained on the filter. The device further comprises channels to remove the micro-organisms from the filter and lyse them in a separate chamber. Alternatively, the device further comprises means for lysing micro-organisms on the filter, and channels to transfer DNA from lysed bacterial or fungal cells from the filter to a separate chamber. The device can further contain a DNA purification and detection chamber (5) for assaying the presence of DNA. Typically the detection chamber is a PCR module.

Figure 12:
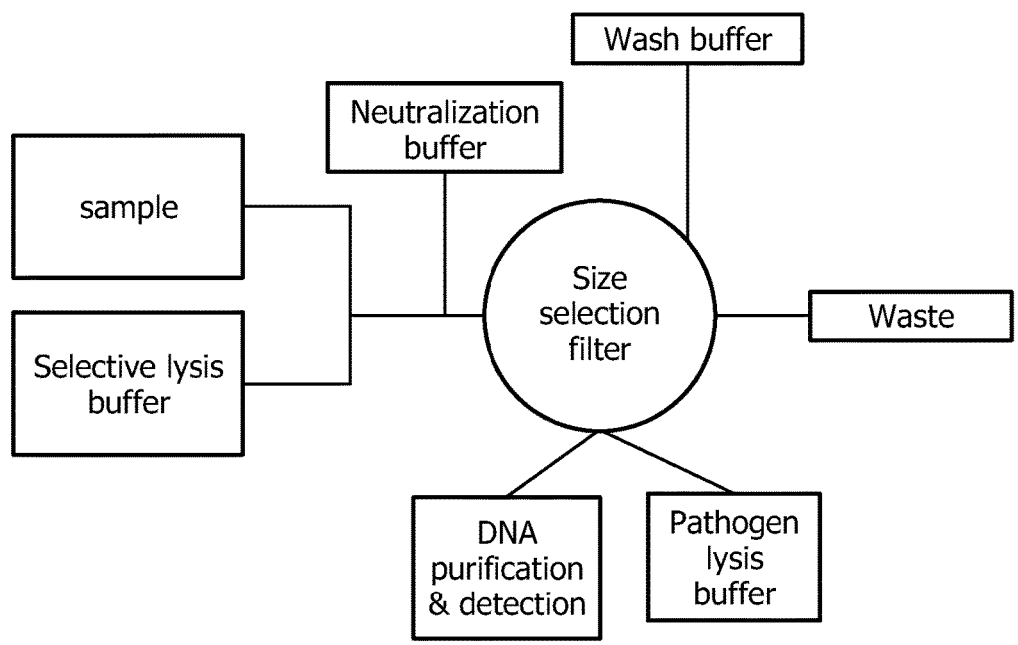
FIG. 12 shows an example of an integrated device comprising a selective lysis unit as described in embodiments of the present invention In the different figures, the same reference signs refer to the same or analogous elements.

An example of a device wherein selective lysis and subsequent DNA purification and identification takes place is depicted in FIG. 12.

Other arrangements of the systems and methods embodying the invention will be obvious for those skilled in the art.

It is to be understood that although preferred embodiments, specific constructions and configurations, as well as materials, have been discussed herein for devices according to the present invention, various changes or modifications in form and detail may be made without departing from the scope and spirit of this invention.

EXAMPLE 1

Effect of pH on Filtration

The goal of this experiment is to assess the effect of pH of the buffer on filtration efficiency. The buffer capacity was sufficient to obtain a similar pH in the final solution as confirmed by measuring the pH of the final solution using conventional techniques known to the person skilled in the art.

The buffers contained:
1M NaBorate, pH 9.0+1% Triton X-100
1M NaBorate, pH 9.5+1% Triton X-100
1M NaCarbonate, pH 10.0+1% Triton X-100
1M NaCarbonate, pH 10.3+1% Triton X-100
1M NaCarbonate, pH 10.8+1% Triton X-100

1 ml of buffer was mixed with 1 ml full blood and incubated for 3 minutes. Hereafter, the neutralization buffer was added and the mixture was filtered through a size selection filter of 25 mm in diameter and with a pore size of 0.45 μm using a vacuum filtration set-up. The volume of blood that was able to pass the filter before it clogged was measured. Results are shown in FIG. 1. This experiment demonstrates that the final pH value should be around 9.5 or higher to get sufficient volumes of blood filtered for analysis of low concentrations of pathogens.

EXAMPLE 2

The effect of pH of the buffer on the recovery of intact pathogens (*E. coli*) after selective lysis of the blood cells is shown.

Used buffers contained:
1M NaBorate, pH 9.0+1% Triton X-100
1M NaBorate, pH 9.5+1% Triton X-100
1M NaCarbonate, pH 10.0+1% Triton X-100
1M NaCarbonate, pH 10.5+1% Triton X-100

Figure 2:
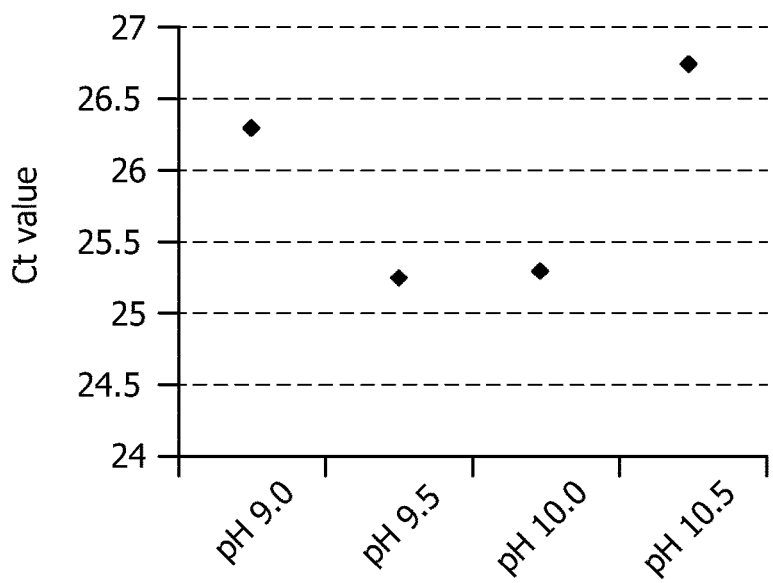
FIG. 2 shows the recovery of different bacteria after lysis at different pH values in accordance with a particular embodiment of methods of the invention.

Identical amounts of bacteria are spiked into 1 ml blood. This volume is treated with the above-mentioned buffers for 3 min. Hereafter the blood is centrifuged (10 min, 4000 g) to collect the intact bacteria. Bacteria are lysed using a standard alkaline lysis method and the DNA is purified using Qiagen spin columns (QiaAmp blood mini kit). The amount of DNA is quantified using real-time PCR. The result is shown in FIG. 2.

The abovementioned figure shows the recovery of the bacteria as a function of the pH of the selective lysis buffer. At low pH values, the white blood cell DNA is not degraded and is inhibiting the PCR reaction. At high pH values, the bacteria start to be lysed during the selective lysis and they are not recovered.

EXAMPLE 3

Influence of incubation time on recovery of pathogens.

Figure 3:
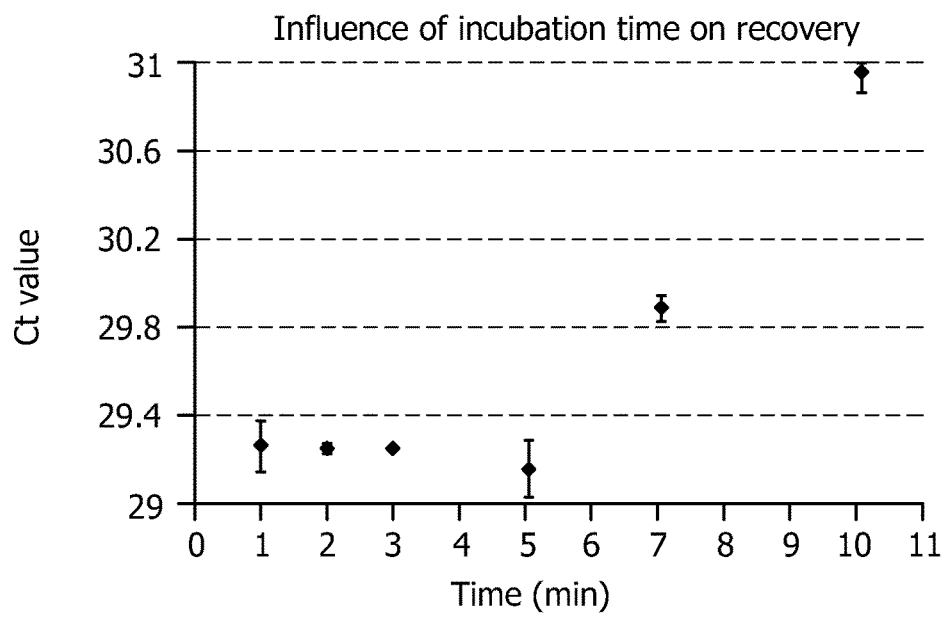
FIG. 3 shows the recovery of different bacteria after lysis at different incubation times in accordance with a particular embodiment of methods of the invention.

This example demonstrates the influence of prolonged incubation of blood with the selective lysis buffer according to the invention on the recovery of intact pathogens. A fixed number of *P. aeruginosa* bacteria was spiked into blood. 1 ml of spiked blood was mixed with 1 ml selective lysis buffer (1M NaCarbonate pH 10.0+1% Triton X-100) and incubated for 1, 2, 3, 5, 7 or 10 minutes. Hereafter, 1 ml of neutralization buffer was added. The pathogens were collected by centrifugation (10 min at 4000 g) and the bacterial pellet was washed. Finally, the cells were lysed by standard alkaline lysis followed by DNA purification using the QiaAmp blood mini kit. The amount of recovered DNA was measured by real-time PCR. Results are visualized in FIG. 3 and indicate that incubation preferably is performed between 30 seconds and 10 minutes.

EXAMPLE 4

Figure 4:
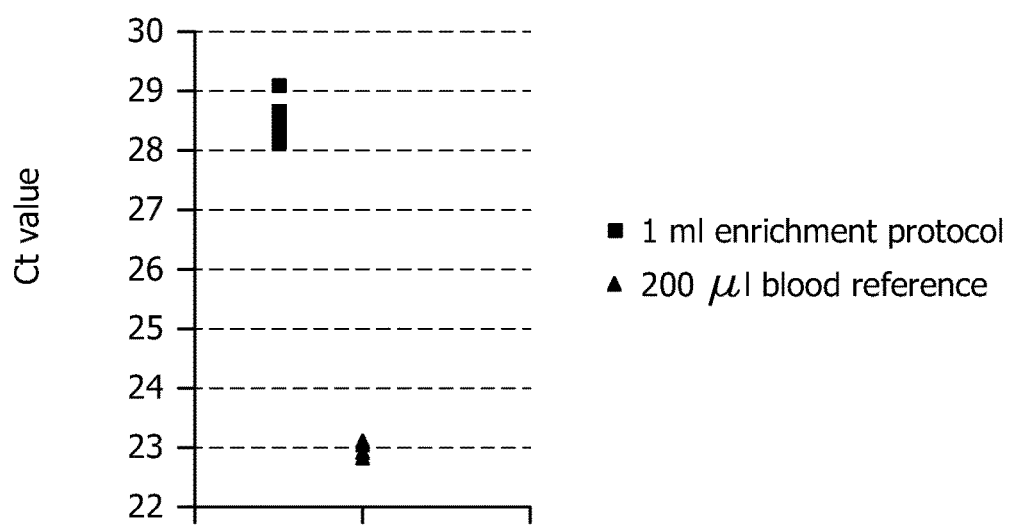
FIG. 4 shows reduction of human background DNA by selective lysis according to the present invention.

Reduction of human background by selective lysis according to the present invention Reduction of the amount of eukarytotic cell DNA, more specifically white blood cell DNA in the current method is important since when present, it will inhibit a following PCR reaction to detect pathogen DNA or RNA. To test for the amount of remaining background DNA, different blood samples are processed with the selective lysis protocol according to the present invention and the amount of white blood cell DNA in the PCR reaction is analyzed using the RNaseP detection kit (Applied Bio systems). The Ct values of these samples are compared with those obtained from 200 μl blood full blood samples, where all white blood cell DNA was present. From literature it is known that the human DNA originating from 200 μl full blood is the maximum amount of background DNA that can be tolerated by a PCR reaction without inhibition of the pathogen DNA amplification. The result of the different PCR reactions is shown in FIG. 4.

This figure shows the difference in amount of human background between the 1 ml processed blood samples according to the method of the present invention ((1 M NaCarbonate pH 10.0+1% Triton X-100) and 200 µl full blood reference samples. Different samples are processed and the PCR results are shown as individual data points. These results demonstrate that the amount of background DNA is much lower (=higher Ct values) in the 1 ml samples processed according to the present invention as compared to the 200 µl full blood reference samples. This result proves that the white blood cell DNA is efficiently and sufficiently removed from the sample when using the method according to the present invention.

EXAMPLE 5

The goal of this example is to demonstrate the detection of the different types of pathogens from full blood by using the method according to the present invention. The different types of pathogens, a gram-negative (*P. aeruginosa*), gram-positive (*S. aureus*) and fungi (*C. albicans*) were mixed together into 1 ml blood. The blood sample was treated with the selective lysis buffer (1 ml of a 1M NaCarbonate pH 10.0+1% TX-100 solution) for 3 min followed by neutralization of the pH and filtration using a size selection filter with sufficiently small pores to retain all cells. The filter was washed to remove the remaining inhibitors such as hemoglobin and DNA of the white blood cells. Hereafter, the cells were lysed following a standard alkaline lysis protocol and the DNA was purified using the Qiagen blood mini kit.

Figure 5:
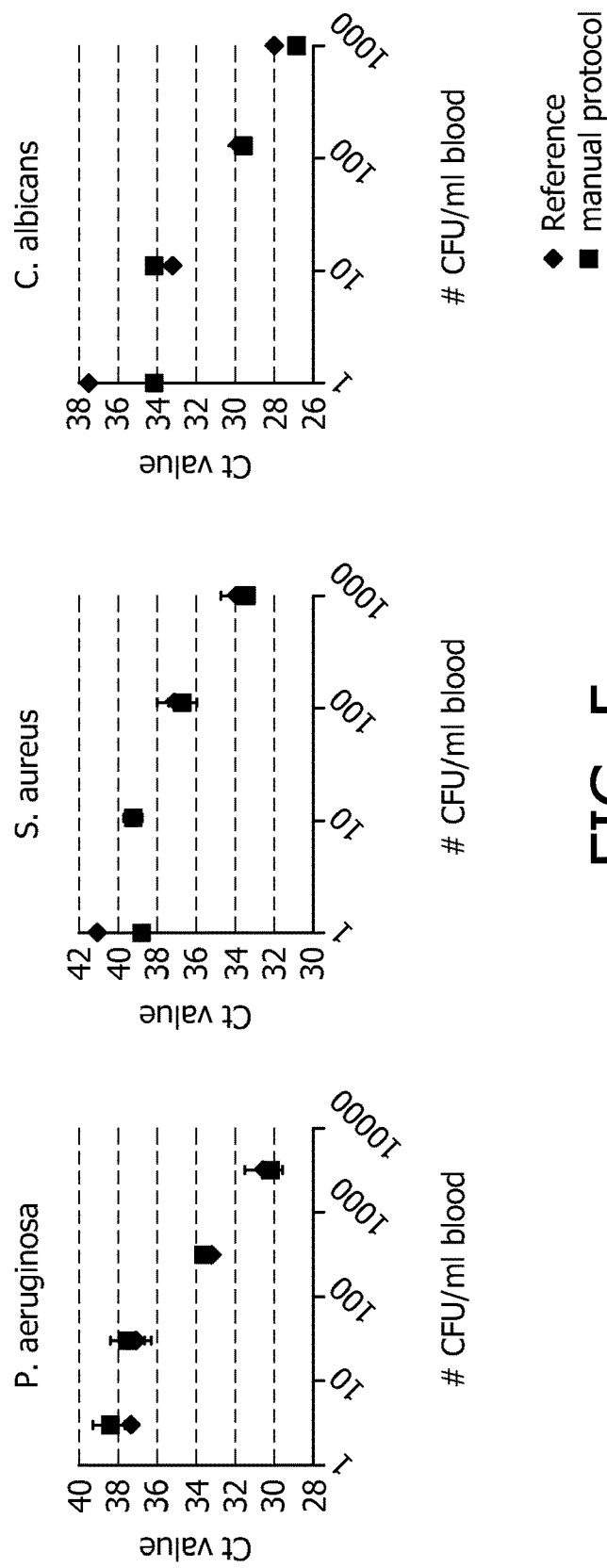
FIGS. 5 and 6 show detection of different types of pathogens in 1 and 5 ml full blood respectively.

The pathogenic DNA was detected by real-time PCR; the Ct value is a measure for the amount of DNA. For quantification a small part of the spiked blood sample was plated on blood agar plate to obtain the CFU count. The data as present in FIG. 5 show that it is possible to detect low numbers of pathogens from full blood. The reference sample contains the same number of bacteria in a small volume of PBS buffer which is directly lysed, followed by DNA purification and quantification using real time PCR. The reference measurements and the actual enrichment experiments from blood gave similar Ct values, thus demonstrating the high recovery rates. The negative control (blood without bacteria) shows no PCR signal.

Figure 6:
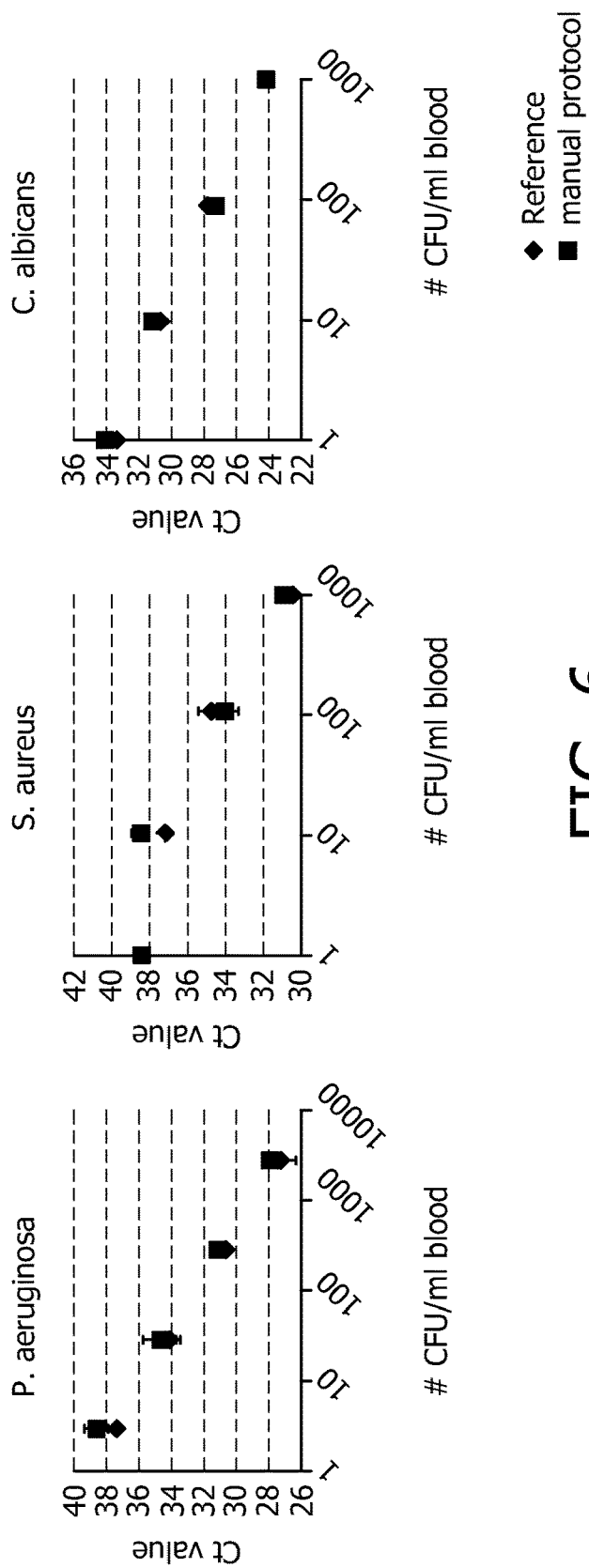

The assay allows larger volumes of blood to be used. The experimental set-up is identical to the previous example but the amount of blood is increased to 5 ml. The reference sample contains the same number of pathogens as the 5 ml blood sample but the cells remain in a small volume of PBS and are directly lysed. The results are represented in FIG. 6.

This experiment demonstrates the possibility to recover low number of pathogens from large volumes of blood. The data show that the concentration of recovered pathogen DNA is similar to the reference. Therefore it can be concluded that the majority of the pathogens remain intact during the selective lysis and the reduction in the white blood cell DNA is effective to prevent inhibition of the pathogen PCR.

EXAMPLE 6

Figure 7:
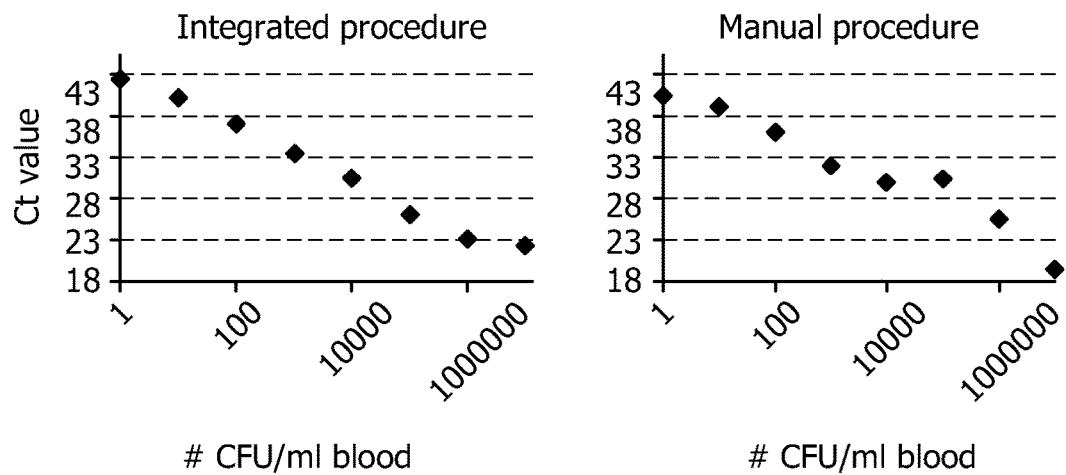
FIG. 7 shows a comparison between manual and device performed method according to the present invention.

The selective lysis method according to the present invention may be performed in various ways, not limited to but including a manual procedure and a procedure wherein the method is performed by a device according to the present invention (integrated procedure). The present example compares such an integrated procedure and a manual procedure. The manual procedure requires manual pipetting and centrifugation steps while the integrated procedure uses a micro-fluidic cartridge and a size selection filter, capable of performing all the required operations. The basic biochemical protocol is similar: selective lysis of the white and red blood cells using a 1M NaCarbonate+1% Triton X-100 solution followed by a neutralization step after 3 min. In the next step the mixture is either centrifuged (manual) or filtered (integrated) and the cells are washed and finally the DNA is released by means of a standard alkaline lysis procedure. In a last step, the DNA is purified using the Qiagen blood mini kit and detected by real-time PCR. The results of the integrated and manual procedure can be found in the following FIG. 7. Comparable results are achieved, demonstrating that the result is independent of the implementation format of the assay.

EXAMPLE 7

In this example, the method according to the present invention is benchmarked against a commercially available method namely the MolYsis Complete kit (Molzym). This kit uses chaotropic agents and detergents to lyse selectively mammalian cells. This lysis step is followed by a digest with a DNAse which is not affected by this chaotropic agent/detergent.

Figure 8:
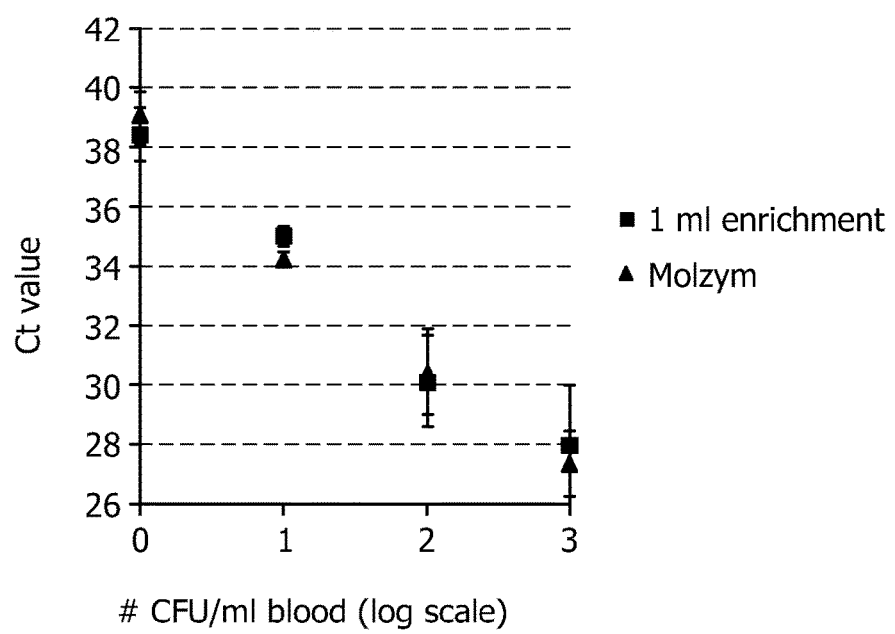
FIG. 8 shows comparison of the method according to the invention to commercially available sepsis detection test

For this experiment, 1 ml blood samples were spiked with different concentrations of *S. aureus*. 1 ml blood was processed as described in Example 5 and another 1 ml was processed with the MolYsis kit according to the manufacturer's instructions. The Ct values are plotted against the concentration of cells in FIG. 8 and show that the method according to the present invention is at least as efficient as the known MolYsis kit without the addition of enzymes or chaotroptic salts.

EXAMPLE 8

After selective lysis of blood cells and enrichment of the pathogen cells on the size selection filter, alkaline lysis was employed to achieve simultaneous lysis of different pathogens on the filter to make the DNA available for PCR analysis.

Figure 9:
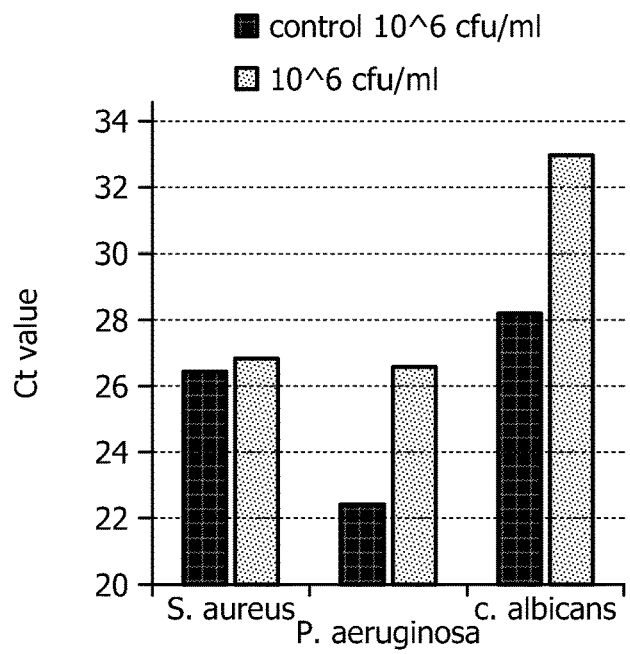
FIG. 9 shows lysis of pathogens after selective lysis and capture on filter according to the present invention.

FIG. 9 shows the result of the alkaline lysis procedure performed on an integrated cartridge. 1 ml of blood was spiked with $10^6$ cells of *S. aureus, P. aeruginosa* and *C. albicans*. After selective lysis of blood cells and enrichment of pathogens on the filter, alkaline lysis was performed, using 200 µl of a solution containing 200 mM NaOH, 0.5% SDS which is incubated at 95° C. for 10 min to obtain complete lysis of the pathogens in the filter. The eluates containing the pathogen DNA were neutralized with 20 µl of a 1 M citric acid solution and purified using the QIAamp DNA/Blood Mini kit. As a control sample, $10^6$ cells of each pathogen were lysed on the bench, neutralized and purified as described above.

Figure 10:
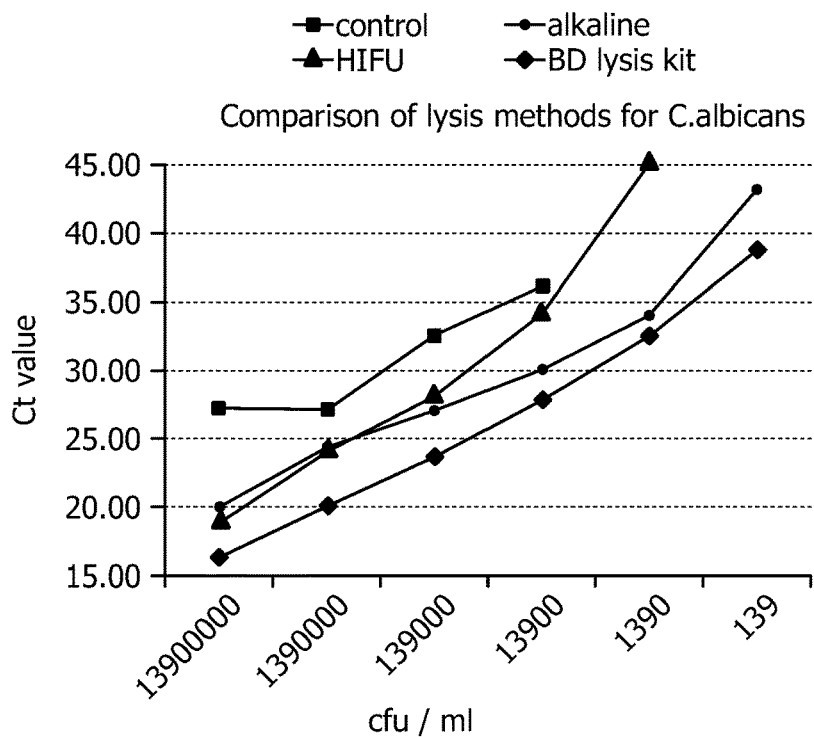
FIG. 10 shows pathogen lysis efficiency in comparison to other lysis methods when performed after selective lysis and capture on filter according to the present invention.

For optimization and benchmarking of the alkaline lysis procedure, *Candida albicans* was chosen as model system since these yeast cells are well known for their rigid cell walls which are difficult to lyse. FIG. 10 compares the alkaline lysis procedure (using 50 mM NaOH, 0.25% SDS in combination with heat treatment) with other lysis methods, namely high intensity ultrasound (HiFU) treatment and a commercial kit (BD GeneOhm lysis kit). For alkaline lysis and lysis by the commercial kit, the samples were concentrated from 1 ml to 160 and 100 µl, respectively, using centrifugation. For HiFU 2 ml of cell solution was used, without prior concentration. After lysis, unlysed cells and debris were removed from the sample by centrifugation. 1 µl of crude lysate was used as input for the PCR.

The combination of NaOH and SDS is more effective for lysis than each of the individual compounds. An increase of the concentration of either compound did not further increase the lysis efficiency. Alkaline lysis without a heat incubation step is significantly less efficient. Lysis efficiency can be increased by incubation for 2 min at 95° C., however, for integration of the assay into a cartridge incubation for a longer time at 70° C. is preferred.

For alkaline lysis cells were resuspended in 100 µA of a lysis solution containing 50 mM NaOH and 0.25% SDS. Subsequently the samples were incubated for 10 min at 70° C., cooled quickly to room temperature and neutralized by addition of 30 µl 500 mM Tris-HCl, pH 7.0 (yielding a final concentration of 150 mM Tris, i.e. 3 times the NaOH concentration).

For crude lysate PCR, unlysed cells and debris were removed from the sample by centrifugation (5 min, 14,000 g). 1 µl of supernatant was added to a 25 µl PCR reaction. Detection by PCR was based on a Taqman PCR assay targeting the rRNA gene (Apollo). The PCR reaction was conducted in Taqman Universal mastermix (Applied Biosystems), using 500 nM forward primer and 300 nM reverse primer and FAM-BHQ1 labelled probe (all oligonucleotides custom synthesized by Biolegio BV). The PCR reaction was performed in a Biorad CFX real-time PCR system. After an initial heating step of 10 min at 95° C. to activate the hot-start polymerase, 50 cycles of 15 sec at 95° C. and 1 min at 60° C. were used for amplification. Fluorescence signals were detected in each cycle during the 60° C. step. Data analysis was performed with the Biorad CFX software.

The invention claimed is:

1. A method for detecting the presence of micro-organisms contained or suspected to be contained within a mammalian blood sample, the method comprising the steps of:
    providing the mammalian blood sample containing or suspected to contain the micro-organisms, wherein:
        said mammalian blood sample comprises whole blood that has not been cultivated, said whole blood including blood plasma and eukaryotic blood cells,
        said mammalian blood sample has a volume between 1 ml and 20 ml,
        said micro-organisms are selected from the group consisting of bacteria and fungi, and
        there are less than 10,000 micro-organisms per milliliter of the mammalian blood sample,
    adding a selective lysis buffer at a selected concentration to the mammalian blood sample to obtain a final solution having a pH level of around 9.5 or higher, said selective lysis buffer including (i) a non-ionic detergent and (ii) an alkaline buffer, said non-ionic detergent present in a concentration of between 0.1% and 5% (w/v % or v/v %),
        wherein the selected concentration of the selective lysis buffer in the final solution is a concentration that achieves said pH level of around 9.5 or higher for the final solution, with a volume of the selective lysis buffer that is between 200% and 10% of a volume of the mammalian blood sample;
    incubating the final solution in the presence of the selective lysis buffer for a time period sufficiently long to selectively lyse the blood cells in the mammalian blood sample while keeping the micro-organisms intact, thereby forming a lysed sample, wherein the percentage of micro-organism cells that remain intact in the lysed sample is at least two times higher than the percentage of blood cells that remain intact in the lysed sample; and
    detecting the presence of the micro-organisms without cultivation of the micro-organisms within said mammalian blood sample.

2. The method according to claim 1, wherein said time period for the incubating step is between 30 seconds and 10 minutes.

3. The method according to claim 1, wherein the non-ionic detergent is selected from the group consisting of Nonidet P40, deoxycholate, lgepal CA 630, Triton-X 100, and any combinations thereof.

4. The method according to claim 1, further comprising centrifuging the incubated final solution and isolating the micro-organisms.

5. The method according to claim 1, further comprising filtering the incubated final solution on a filter with a pore size that retains micro-organisms on the filter.

6. The method according to claim 1, further comprising lysing the micro-organisms.

7. The method according to claim 6, further comprising using a nucleic acid based molecular assay on the lysed micro-organisms.

8. The method according to claim 1, wherein the method further comprises:
    adding an acid or acidic buffer to neutralize the lysed sample.

9. The method according to claim 8, wherein the lysed sample is neutralized to a pH in a range between 7 and 9.

* * * * *